United States Patent
McNeal

(10) Patent No.: US 9,655,783 B2
(45) Date of Patent: May 23, 2017

(54) STRAP ATTACHMENT SYSTEMS AND GOGGLES INCLUDING SAME

(71) Applicant: Smith Optics, Inc., Ketchum, ID (US)

(72) Inventor: Joseph R. McNeal, Hailey, ID (US)

(73) Assignee: Smith Optics, Inc., Portland, OR (US)

( * ) Notice: Subject to any disclaimer, the term of this patent is extended or adjusted under 35 U.S.C. 154(b) by 239 days.

(21) Appl. No.: 13/794,315

(22) Filed: Mar. 11, 2013

(65) Prior Publication Data
US 2014/0250573 A1    Sep. 11, 2014

(51) Int. Cl.
A61F 9/02    (2006.01)

(52) U.S. Cl.
CPC .................... A61F 9/027 (2013.01)

(58) Field of Classification Search
CPC ................. A61F 9/025; A61F 9/027
USPC ..................... 2/426, 436; D16/339
See application file for complete search history.

(56) References Cited

U.S. PATENT DOCUMENTS

| | | | |
|---|---|---|---|
| 860,322 A | 7/1907 | Paroubek | |
| 2,804,623 A * | 9/1957 | Hirschmann | 2/445 |
| 2,903,700 A * | 9/1959 | Finken et al. | 2/10 |
| 3,216,023 A | 11/1965 | Morgan | |
| 3,237,203 A | 3/1966 | Nielsen | |
| D213,085 S | 1/1969 | Wyckoff | |
| 3,691,565 A | 9/1972 | Galonek | |
| 3,783,452 A | 1/1974 | Benson et al. | |
| 4,042,974 A | 8/1977 | Morgan et al. | |
| 4,136,403 A | 1/1979 | Walther et al. | |
| D266,626 S | 10/1982 | Gooding | |
| 4,527,291 A * | 7/1985 | Nussbickl | 2/450 |
| 4,686,712 A | 8/1987 | Spiva | |
| 4,713,844 A | 12/1987 | Westgate | |
| 4,716,601 A * | 1/1988 | McNeal | 2/434 |
| 4,764,989 A | 8/1988 | Bourgeois | |
| 4,918,753 A | 4/1990 | Mermillod | |

(Continued)

FOREIGN PATENT DOCUMENTS

FR    2838307 A1    10/2003
JP    2000-239916 A    9/2000

(Continued)

OTHER PUBLICATIONS

International Search Report and Written Opinion dated May 23, 2012 for PCT Application No. PCT/US2011/055726.

(Continued)

*Primary Examiner* — Richard Quinn
*Assistant Examiner* — Anne Kozak
(74) *Attorney, Agent, or Firm* — Dorsey & Whitney LLP

(57) ABSTRACT

Examples of strap attachment systems and goggles including same are described. Goggles according to the present examples may include a lens, a strap connector attached to the lens, and a strap including an attachment portion configured to be removably coupled to the strap connector. The strap connector may be fixedly or removably attached to the lens, and in certain examples the strap connector is pivotally coupled to the lens. A strap connector according to some examples herein includes a first molded body including a passage and a second molded body including a post, the passage configured to engage the post when inserted into the passage to secure the connector to the lens.

17 Claims, 11 Drawing Sheets

(56) References Cited

U.S. PATENT DOCUMENTS

| | | | |
|---|---|---|---|
| 5,213,241 A * | 5/1993 | Dewar | A45C 11/04 206/5 |
| 5,363,512 A * | 11/1994 | Grabos et al. | 2/436 |
| 5,410,763 A * | 5/1995 | Bolle | 2/436 |
| D372,928 S * | 8/1996 | Brune et al. | D16/311 |
| 5,592,698 A * | 1/1997 | Woods | 2/424 |
| 5,689,834 A * | 11/1997 | Wilson | 2/436 |
| 5,760,867 A * | 6/1998 | Pernicka et al. | 351/120 |
| D400,555 S | 11/1998 | Wang | |
| 5,845,341 A | 12/1998 | Barthold et al. | |
| 5,867,841 A * | 2/1999 | Chiang | 2/436 |
| 5,987,652 A | 11/1999 | Fowler | |
| 6,047,410 A * | 4/2000 | Dondero | 2/426 |
| D428,906 S | 8/2000 | Bolle | |
| 6,276,795 B1 * | 8/2001 | Hall et al. | 351/62 |
| D455,522 S | 4/2002 | Royes et al. | |
| D464,174 S | 10/2002 | Lu | |
| 6,490,729 B1 | 12/2002 | Dondero | |
| D477,010 S * | 7/2003 | Moritz et al. | D16/312 |
| D482,500 S | 11/2003 | Ho | |
| 6,708,340 B1 | 3/2004 | Dondero | |
| 6,715,157 B2 * | 4/2004 | Mage | 2/439 |
| 6,845,548 B1 | 1/2005 | Lin | |
| 6,970,691 B2 | 11/2005 | Thompson | |
| D515,615 S * | 2/2006 | Fecteau et al. | D16/312 |
| D535,059 S | 1/2007 | Lam | |
| 7,260,850 B2 | 8/2007 | Ambuske et al. | |
| D556,951 S | 12/2007 | Gath | |
| D610,602 S | 2/2010 | Yun | |
| D616,915 S | 6/2010 | Silveria et al. | |
| D628,346 S | 11/2010 | Petzl | |
| D645,210 S | 9/2011 | Chilson et al. | |
| D655,048 S | 2/2012 | Moeller et al. | |
| D675,249 S * | 1/2013 | Giroux | D16/339 |
| D698,854 S * | 2/2014 | McNeal | D16/312 |
| D700,929 S * | 3/2014 | McNeal | D16/312 |
| D710,930 S * | 8/2014 | McNeal | D16/312 |
| 9,072,331 B2 | 7/2015 | McNeal | |
| 2005/0183190 A1 | 8/2005 | Hussey | |
| 2006/0059606 A1 | 3/2006 | Ferrara | |
| 2007/0083967 A1 | 4/2007 | Crossman et al. | |
| 2007/0130672 A1 | 6/2007 | Beddoe et al. | |
| 2008/0052808 A1 | 3/2008 | Leick et al. | |
| 2008/0172778 A1 * | 7/2008 | Lysogorski | 2/436 |
| 2008/0256688 A1 * | 10/2008 | Bruce | 2/441 |
| 2008/0301857 A1 * | 12/2008 | Wang-Lee | 2/431 |
| 2008/0301858 A1 * | 12/2008 | Wang-Lee | 2/436 |
| 2009/0268153 A1 * | 10/2009 | Wang-Lee | 351/155 |
| 2009/0300830 A1 * | 12/2009 | Mage | 2/441 |
| 2010/0064421 A1 * | 3/2010 | Wang-Lee | 2/428 |
| 2010/0325784 A1 | 12/2010 | Abbott et al. | |
| 2011/0072564 A1 | 3/2011 | Krauter | |
| 2011/0113535 A1 | 5/2011 | Lebel et al. | |
| 2011/0258759 A1 * | 10/2011 | Renaud-Goud et al. | 2/428 |
| 2011/0265237 A1 | 11/2011 | Lazar et al. | |
| 2012/0180202 A1 | 7/2012 | McNeal | |
| 2012/0180203 A1 * | 7/2012 | Giroux et al. | 2/422 |
| 2012/0185989 A1 | 7/2012 | Higgins | |
| 2013/0019387 A1 * | 1/2013 | McNeal | 2/436 |
| 2014/0115761 A1 * | 5/2014 | McNeal et al. | 2/439 |

FOREIGN PATENT DOCUMENTS

| | | |
|---|---|---|
| KR | 10-0918879 B1 | 9/2009 |
| WO | 2008/006357 A2 | 1/2008 |
| WO | 2009/092368 A2 | 7/2009 |
| WO | 2010/076817 A1 | 7/2010 |
| WO | 2012/099631 A1 | 7/2012 |

OTHER PUBLICATIONS

English Machine Translation of FR 2838307 A1 via http://www.espacenet.com.

Examiner's Report for CA application No. 2,823,931 dated Nov. 7, 2014.

Office action dated Apr. 24, 2015 issued for Canadian Appln No. 2,843,692.

"Examiner's Report received for Canadian Patent Application No. 2,843,692 dated Mar. 31, 2016".

* cited by examiner

STRAP ATTACHMENT SYSTEMS AND GOGGLES INCLUDING SAME

TECHNICAL FIELD

Examples described herein relate to eyewear, and more particularly to goggles including a strap attachment system adapted for removable attachment of a goggle strap thereto, for example, to enable the use of the goggle lens with any of a plurality of straps.

BACKGROUND

Protective eyewear, such as goggles are frequently worn by a user when participating in sports (e.g., skiing, riding, sky-diving, etc.) and/or when the user is in a hazardous environment (e.g., various industrial or combat settings). Protective eyewear is commonly worn to provide eye protection for the user from debris, projectiles, sharp objects, or objects and impact that can cause eye injury.

Certain low profile goggles (e.g., jockey goggles) consist of a single flexible lens and an elastic strap attached to the lens. The lens, which may have foam or rubberized rim portion around the perimeter of the lens, is tensioned against the rider's face using the elastic strap. The lens is sufficiently flexible to allow it to contour against the user's face and the rim portion forms a seal with the user's face. However, a flexible lens as is generally used in conventional low profile goggles may not provide sufficient eye protection in certain situations (e.g., against ballistics or certain kinds of debris). Furthermore, flexing the lens may result in optical distortion. Moreover, the strap, which is typically made from silicon, rubber, or other elastic material, is typically permanently attached to the lens. As such, in the event that the strap becomes unusable (stretched-out) or damaged, replacement of the whole goggle, including the lens, may be required even though the lens may be in working condition.

The examples according to the present invention may address some or all of the shortcomings of conventional goggles of this kind and/or may provide further advantages as will be appreciated in light of this disclosure.

BRIEF DESCRIPTION OF THE DRAWINGS

The above and still further objectives, features, aspects and attendant advantages of the present invention will become apparent from the following detailed description of certain preferred and alternate embodiments and method of manufacture and use thereof constituting the best mode presently contemplated of practicing the invention, when taken in conjunction with the accompanying drawings, in which.

DETAILED DESCRIPTION

Certain details are set forth below to provide a sufficient understanding of embodiments of the invention. However, it will be appreciated by one skilled in the art that some embodiments may not include all details described.

The present disclosure is related to goggles and strap attachment systems and methods for removably attaching a strap to a goggle. Goggles according to the present disclosure include a lens structure, which may be a single lens or a double lens structure. The lens structure may be attached, fixedly or removably, to a frame which is adapted for a conformal fit against the wearer's face. In other examples, the goggle may not include a frame and the lens structure may be otherwise adapted for conformal fit against the user's face as will be further described. A strap or a plurality of straps may be attached to the lens structure and/or frame at opposite ends of the frame or lens structure. In some examples, a single strap may be used, and each end of the strap attaches to the lens structure with the strap creating a loop to facilitate securing the frame or lens structure against the user's face. In other examples a separate strap may be secured to each end of the lens structure or frame and the straps may be buckled or otherwise fastened to one another thereby forming a loop for placing around the wearer's head. In yet further examples a pair of straps may be secured to each end of the lens structure and the straps may then be secured to another accessory, for example a helmet or other head gear. Regardless of the type of goggle or strap configuration used, the examples herein may facilitate use of a lens structure with any of a plurality of straps and generally interchangeability of the strap(s) with increased speed and/or ease.

Figure 1:
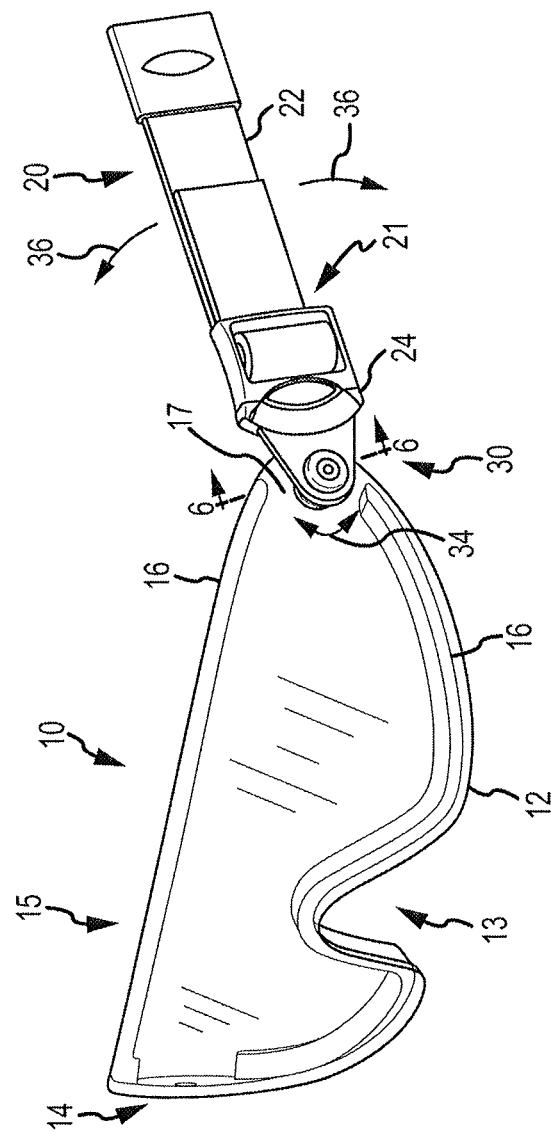
FIG. 1 is an isometric view of a goggle including a strap attachment system according an example of the present disclosure.
Figure 2:
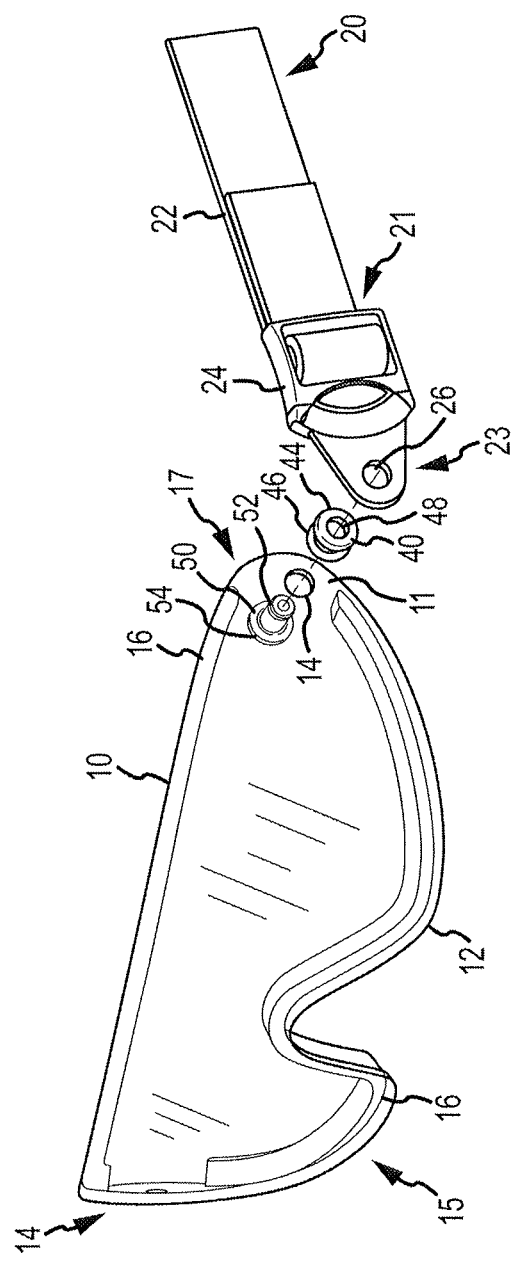
FIG. 2 is an exploded isometric view of the goggle in FIG. 1.
Figure 3:
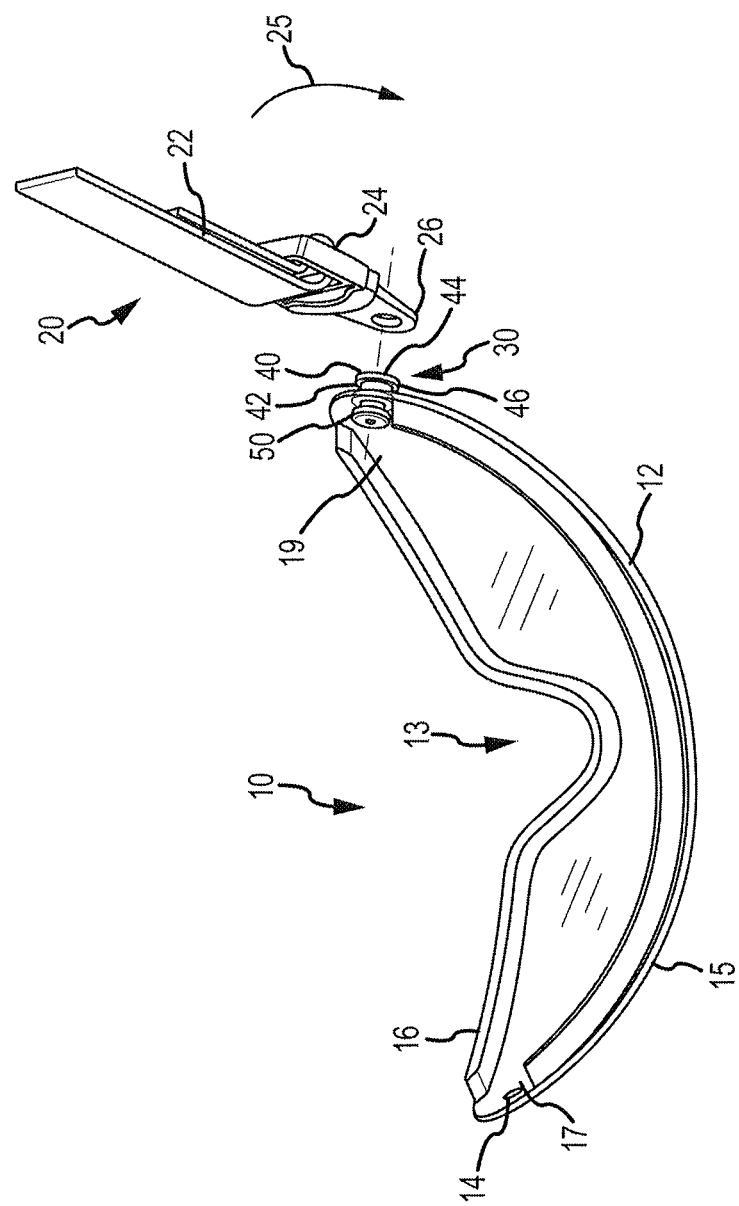
FIG. 3 is an alternate isometric view of the goggle in FIG. 1 depicted with the strap removed from the goggle.

FIG. 1 shows a goggle with a strap attachment system according to one example of the present disclosure. FIGS. 2 and 3 show additional views of the goggle according to the example in FIG. 1. The goggle includes a lens structure 10, a strap 20, and a strap connector 30. The lens structure 10, which in the example is a FIG. 1 is implemented as a single lens 12. The lens 12 may be generally oval in shape so as to extend across the field of view of the user (interchangeably referred to herein as wearer). One or more recesses may be formed (e.g., nose recess 13) to accommodate features of the wearer's face (e.g., the wearer's nose). Further contouring of the lens (e.g., by shaping the outer perimeter of the lens) may be used for achieving additional utilitarian and aesthetic advantages. The lens 12 may include a hole 14 on each side of the lens for securing the strap thereto, as will be further described. The lens may be made from any suitable transparent material as known in the art and/or may include any of a variety of coatings (e.g., anti-glare, scratch-resistance, polarization coating, etc.). The lens 12 may be made from an impact resistant material which may be sufficiently hard so as to withstand damage to the lens from projectiles. As such, lenses according to some examples herein may be more rigid than lenses frequently used in similar low profile goggle (e.g., conventional jockey goggles), which are typically configured to flex against the user's face.

The lens 12 includes one or more contact members 16 which are attached to the lens 12 along the perimeter portion 15 of the lens 12. In some examples, the one or more contact members 16 may be adhered to the lens, for example using a permanent pressure sensitive adhesive or an epoxy. The one or more contact members 16 may extend along a substantial portion of the perimeter including the nose recess 13, but need not extend fully around the perimeter of the lens to provide the desired functionality of cushioning the lens against the user's face. The one or more contact members 16 are configured to provide a conformal yet comfortable fit against the wearer's face. The one or more contact members 16 may be made from a compliant material. For example, the contact members 16 may be made of foam, rubber, silicone, or other soft material, which may be selected for its ability to conform to the contours of the wearer's face while still having sufficient stability to function as a spacer between the user's face and the lens. The contact members 16 may be generally elongate members with a rounded or rectangular cross section. In some examples, the contact members 16 may be one or more strips of foam with an adhesive layer on one side of the foam, which adhesive layer is used to secure the foam to the lens. In further examples, the cross section of the contact member may vary along its length (e.g., as shown in the example in FIG. 8). In such examples, the contact member may be molded so as to provide a more customized fit.

In other examples, the lens 12 may instead be provided in a frame (not shown), which may be removably or fixedly attached to the lens. The frame may be formed of a combination of compliant and resilient materials and operably configured to serve as the spacer between the lens and the user's face. Goggle frames removably or fixedly attached to the lens structure are generally known in the art and will not be described in further detail herein, however it will be understood that any number of conventional goggle frames may be used with the examples herein.

The strap 20 may be made from a flexible material and may include an attachment portion configured to be removably coupled to the strap connector 30, which is described in further detail below. The strap 20 may include a band 22 and a strap tab 24 as shown in FIG. 1. However, in some examples, the band 22 and strap tab 24 may be a unitary component (e.g., made from the same elastic material) and end portions of the strap may be configured as the attachment portions adapted for removable engagement with strap connectors 30 on each side of the lens. For simplicity, only one strap connector 30 on one side of the lens structure 10 is depicted in the example in FIG. 1, however, it will be understood that a second strap connector 30 according to any of the examples herein may be used on the opposite side of the lens structure. In some examples and without departing from the scope of this disclosure, the strap may be attached fixedly at one side of the lens and may be removably attached according to the examples herein on only one side of the lens, for example for quick release of the goggle from the wearer's face.

The band 22 is attached to the strap tab 24 at one end 21 of the strap tab 24, for example by threading the band 22 through a slot or a plurality of slots arranged at the end 21. The band 22 may be made from various materials. For example, the band 22 may be made from an elastic material (e.g. rubber, silicone, stretchable fabric, bungee cord) so that it can be stretched. The band 22 may be made from a non-stretchable material as well, such as a nylon strap. An opening 26 is formed at the end 23 of the strap tab 24, opposite the end 21. The strap tab 24 may be made from a resilient material, such as a rubber, which can be deformed, for example temporarily deformed during use, to facilitate placement of the strap tab 24 over at least a portion of the strap connector 30. That is, during removal and attachment of the strap 20 to the lens structure 10, the strap tab 24 may stretch so that the opening 26 is enlarged sufficiently to permit the opening 26 to pass over the strap connector 30 as will be described.

The strap connector 30 is secured to a side perimeter portion 17 of the lens 12. It will be understood that in some examples, in which the lens 12 is provided in a frame, the strap connector 30 may instead be secured to the structure of the frame in a similar manner as described here with respect to the lens. The strap connector 30 may be permanently attached to the lens (e.g., bonded to or fastened thereto using a non-removable fastener) or it may be removable, for example for replacement of the strap connector 30.

The strap connector 30 in the example in FIG. 1 is configured to be mechanically coupled to the lens 12 through hole 14. The strap connector 30 includes a button element 40 and a post element 50, the post element 50 configured to secure the button element 40 to the lens. Features of the strap attachment system according to the example in FIG. 1 will be described in further detail and with further reference to FIG. 6, which shows a cross section of the attachment system taken along the line 6-6 in FIG. 1. In the cross-section in FIG. 6, the lens 12 has been omitted for clarity of illustration.

The button element 40 may be generally cylindrical in shape and may include a shaft 42 and a retaining flange 44 disposed at one end of the shaft. The diameter of the shaft, $D_S$, may be smaller than the size of the opening 26 (e.g., diameter $D_O$) such that the shaft 42 can pass freely through the opening 26. In this regard, diameter $D_O$ and diameter $D_S$ are sized for a clearance fit between the shaft and opening 26. In contrast, the diameter $D_{RF}$ of the retaining flange is larger than the size of the opening 26. As such, the retaining flange 44 does not pass freely through the opening 26 (e.g., the opening 26 and retaining flange 44 are sized for an interfering fit with one another) and may retain the strap tab 24 on the strap connector 30.

The button element may also include a stop flange 46 disposed at the second end of the shaft 42 opposite the retaining flange 44. The diameter $D_{SF}$ of the stop flange 46 is larger than the diameter $D_H$ of hole 14 such that stop flange 46 retains the button element 40 in position against the outer surface 11 of the lens 12 The diameter of the stop flange may, but need not be, the same as the diameter of the retaining flange 44 so long as the stop flange is sufficiently large to prevent movement of the button element into the hole 14.

The post element 50 includes a post 52 and a head 54, the head being wider than the post 52. The diameter $D_{PH}$ of head 54 is larger than the diameter $D_H$ of hole 14 and the diameter $D_P$ of post 52 is smaller than the diameter $D_H$ of hole 14. As such, post 52 passes freely through hole 14 while the head 54 retains the post element 50 against the inner surface 19 of the lens 12. The button element 40 includes a passage 48 along its longitudinal direction, which passage 48 extends through at least a portion of the interior of shaft 42. The passage 48 may, but need not, extend through the length of the button element 40, as shown in the example in FIG. 6. The passage 48 may have a diameter which is the same or larger than the diameter of post 52. For example, the diameter of passage 48 and diameter of post 52 may be selected for a press fit of post 52 within the passage 48. That is, in some instances, the post element 50 may be retained inside the passage 48 of the button element 40 by way of frictional force. In other examples, the post 52 and/or inner surface of the passage 48 may include features (e.g., cooperating protrusion 56 and indent 58) which are configured to engage when the post 52 is inserted in the passage for securing the post 52 therein. The post 52 may be hollow for allowing the post 52 to temporarily deflect inwardly as the post 52 is snapped into engagement with passage 48. Other mechanisms for securing the post element 50 to the button element 40 may be used.

When assembled, the strap connector 30, including button element 40 and post element 50 may be generally coaxially arranged with the hole 14 of the lens. The button element 40 is disposed adjacent the exterior surface 11 of lens 12 and the post element 50 is disposed adjacent the interior surface 19. The button element may contact the exterior surface 11 and/or the post element 50 may contact the interior surface 19. The strap connector 30 may be pivotally or fixedly attached to the lens. For example, the strap connector 30 may be configured such that it is free to rotate about its center axis 32 within the hole 14. The diameter $D_P$ of post 52 may be smaller than the diameter $D_H$ of hole 14 whereby the post 52 may be pivotally coupled to hole 14. In other examples, the strap connector 30 may be substantially immobilized relative to lens 12. For example, the button element 40 and/or post element 50 may be adhered to respective contacting surfaces of the lens. In other examples, the diameter $D_P$ of post 52 may be sized for a press fit within hole 14. In yet further examples, the post element 50 and button element 40 may be pressed against respective contacting surfaces of the lens 12 thereby immobilizing the strap connector 30 relative to the lens 12, for example by way of friction, or through the use of some other technique. The strap connector 30 being rotatable relative to the lens structure or frame (e.g., as indicated by arrow 34) may be advantageous. For example, a rotatable strap connector 30 provides rotational freedom of the strap 20 relative to the frame/lens structure, which may facilitate pivotal adjustment (e.g., as indicated by arrows 36) of the lens 12 and/or strap 20 on the user's head.

As described above, during use, the user may attach the strap 20 to the strap connector 30 by placing the strap tab 24 over the retaining flange 46 of the strap connector. A portion of the strap tab 24, particularly near the opening 26, may stretch temporarily during the passing of the retaining flange 44 through the opening 26. The strap tab 24 is then retained in engagement with the strap connector 30 by virtue of the retaining flange 44 being larger than the opening 26. When the user wishes to remove the strap, the user pulls the strap and/or strap tab 24 over the retaining flange 44. For example, the strap and/or strap tab 24 may be pulled in a generally outward and/or forward direction (e.g., as indicated by arrow 25 in FIG. 3). The end 21 of the strap tab 24 generally rotates forward in a peeling action to cause the strap tab to release from the retaining flange 44 (e.g., the opening 26 is slightly and temporarily deformed to allow the strap tab 24 to be pulled over the retaining flange 44).

Figure 4:
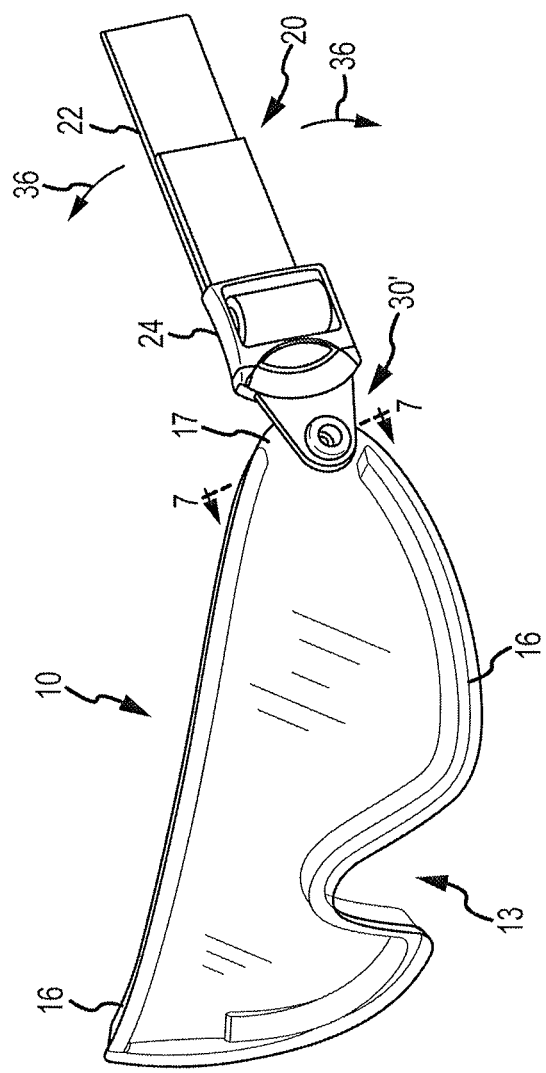
FIG. 4 is an isometric view of a goggle including a strap attachment system according to another example of the present disclosure.
Figure 5:
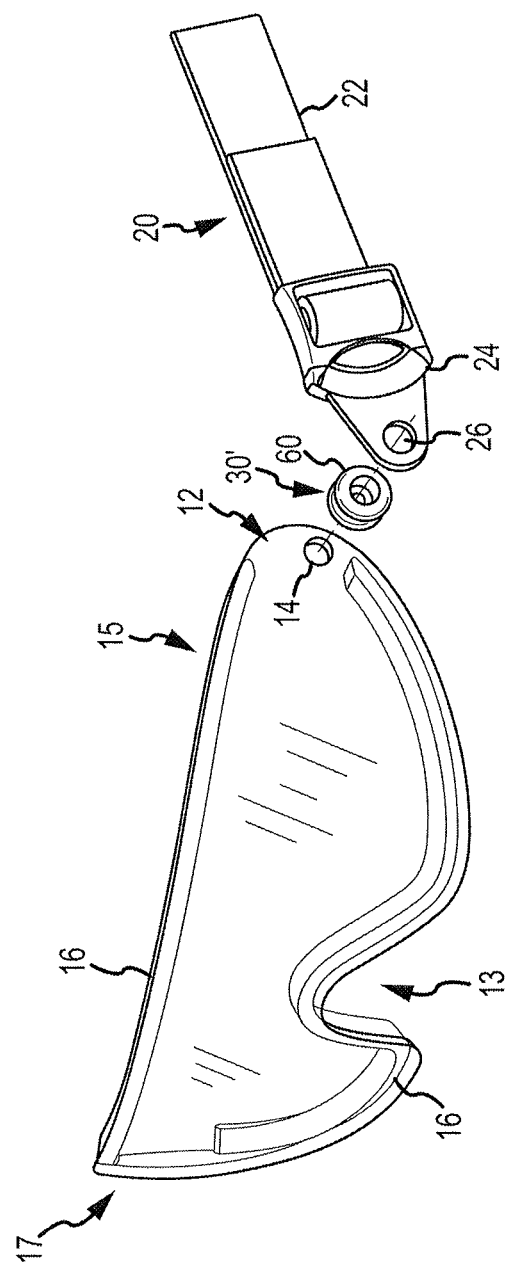
FIG. 5 is an exploded isometric view of the goggle in FIG. 4.
Figure 7:
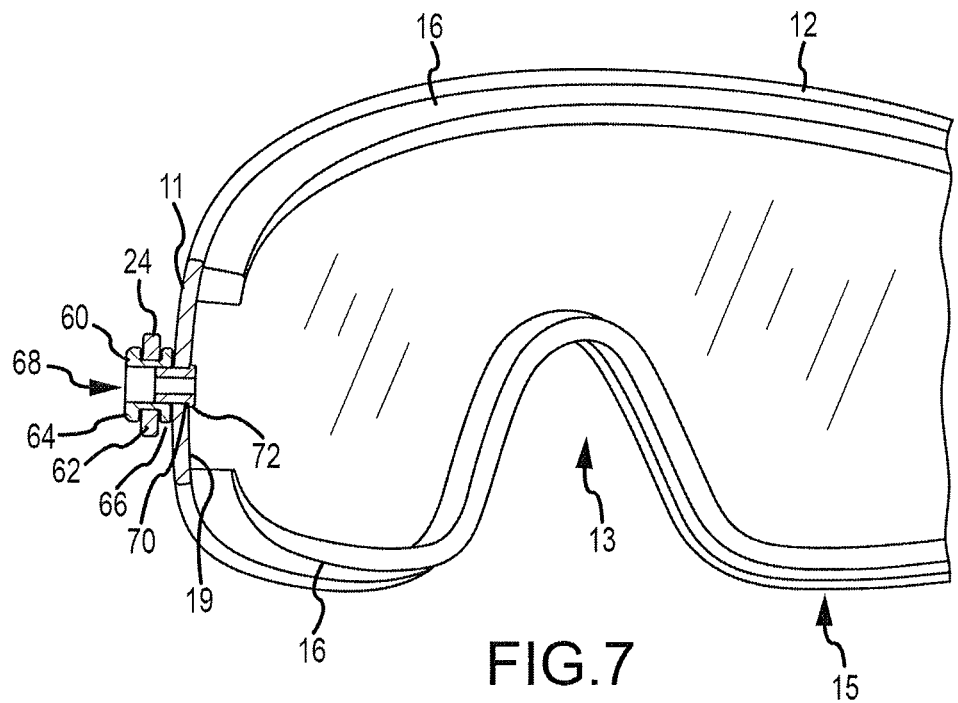
FIG. 7 is a cross section of the strap attachment system according to the example in FIG. 4.

Referring now to FIGS. 4, 5 and 7, another embodiment of a strap attachment system according to the present invention will be described. In the example in FIGS. 4-5, the goggle includes a lens structure 10 and a strap 20 which may be configured similarly to and include some or all of the features as described with respect to the example in FIG. 1. The goggle includes a strap connector 30', which similar to the strap connector 30 is configured for being mechanically coupled to the lens through hole 14. The strap connector 30' includes a button element 60, however in contrast to the example in FIG. 1 the strap connector 30' does not include a post element. Instead, the button element 60 has an anchor portion adapted for attaching the strap connector to the lens as will be described.

Similar to the example in FIG. 1, the button element 60 may include a shaft 62, a retaining flange 64, and a stop flange 66 (see FIG. 7), which may be configured similarly to the shaft 42, retaining flange 44 and stop flange 46, respectively, of the button element 40. An anchor portion 70 extends from the stop flange 66 in the opposite direction of shaft 62. The anchor portion 70 may be implemented as a cylindrical portion having a diameter $D_A$ which is larger in diameter than the diameter $D_H$ of hole 14 for press fitting the anchor portion 70 therein. In other examples, the diameter $D_A$ may be smaller than the diameter $D_H$ to allow the anchor portion to rotate freely within hole 14, with the anchor portion becoming wider at the base 72 to secure and retain the button element 60 within the hole 14. In some examples, the anchor portion 70 may include a plurality of legs or l-shaped features, which can be squeezed towards each other during insertion of the anchor portion through hole 14 and released upon passing through to the opposite side of hole 14. The button element 60 includes a passage 68 along its longitudinal direction, which passage 68 extends through at least a portion of the interior of button element 60. The passage 68 may, but need not, extend through the length of the button element 60. The passage 68 may have the same or varying cross-section. In the particular example in FIG. 7, the passage 68 is narrower along the anchor portion 70 and stop flange 66, the passage 68 being wider along the shaft 42 and retaining flange 64. The button element 60, as well as the button element 40 and button element 60, can be made from virtually any relatively rigid plastic material, such as Nylon or Polystyrene (e.g., PC/ABS blend plastic) materials, and can be fabricated using conventional manufacturing techniques, for example, injection molding techniques.

Other attachment techniques for securing the strap connector 30 or 30' to the lens 12 may also be used. In some examples, a rivet or other conventional fastener (e.g., a threaded fastener), may be inserted through at least a part of the anchor portion 70. The conventional fastener may be made from metal or any other material which is stronger and/or more rigid than the materials used for the strap connectors 30, 30'.

Figure 6:
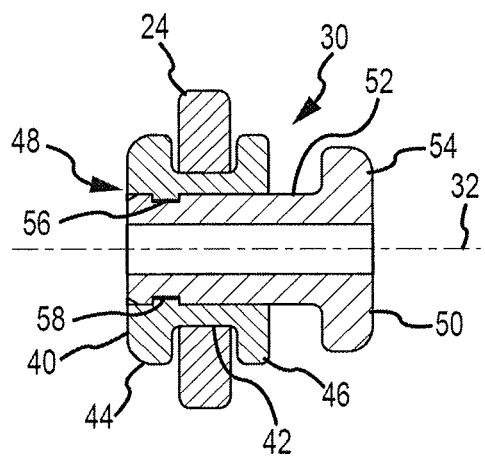
FIG. 6 is a cross-section of the strap attachment system according to the example in FIG. 1.

For example, a conventional fastener (e.g. a rivet or a threaded fastener) may be used instead of or in addition to the post element 50 in the embodiment depicted in FIG. 6. The rivet may be inserted through the passage of post element 50, with the head of the rivet abutting the head 54. The rivet may allow for a more rigid connection between the strap connector 30' and lens 12, for example to ensure that the strap connector does not inadvertently disconnect from the lens during use (e.g. when tension is applied to the strap). In the absence of post element 50, the head of the rivet may abut the inner surface 19 of the lens or a shim (not shown) disposed between the rivet and lens. In the embodiment in FIG. 7, a conventional fastener such as a rivet may be inserted adjacent the base 72 of the anchor portion for enhancing the connection between the strap connector 30' and the lens. Such additional mechanical fasteners (e.g. conventional fastener) may generally provide a more secure or firmer connection of the strap attachment system to the goggle.

In yet further examples, the strap connector 30, 30' may be threadedly secured to the lens. For example, and with reference to the embodiment in FIG. 7, the anchor portion 70 may be provided with threads and the hole 14 may include cooperating threads for threadedly coupling the strap connector 30' thereto. Sonic welding may be used to permanently attach any of the contacting surfaces of connector 30, 30' to the lens as may be suitable for particular applications.

Figure 8:
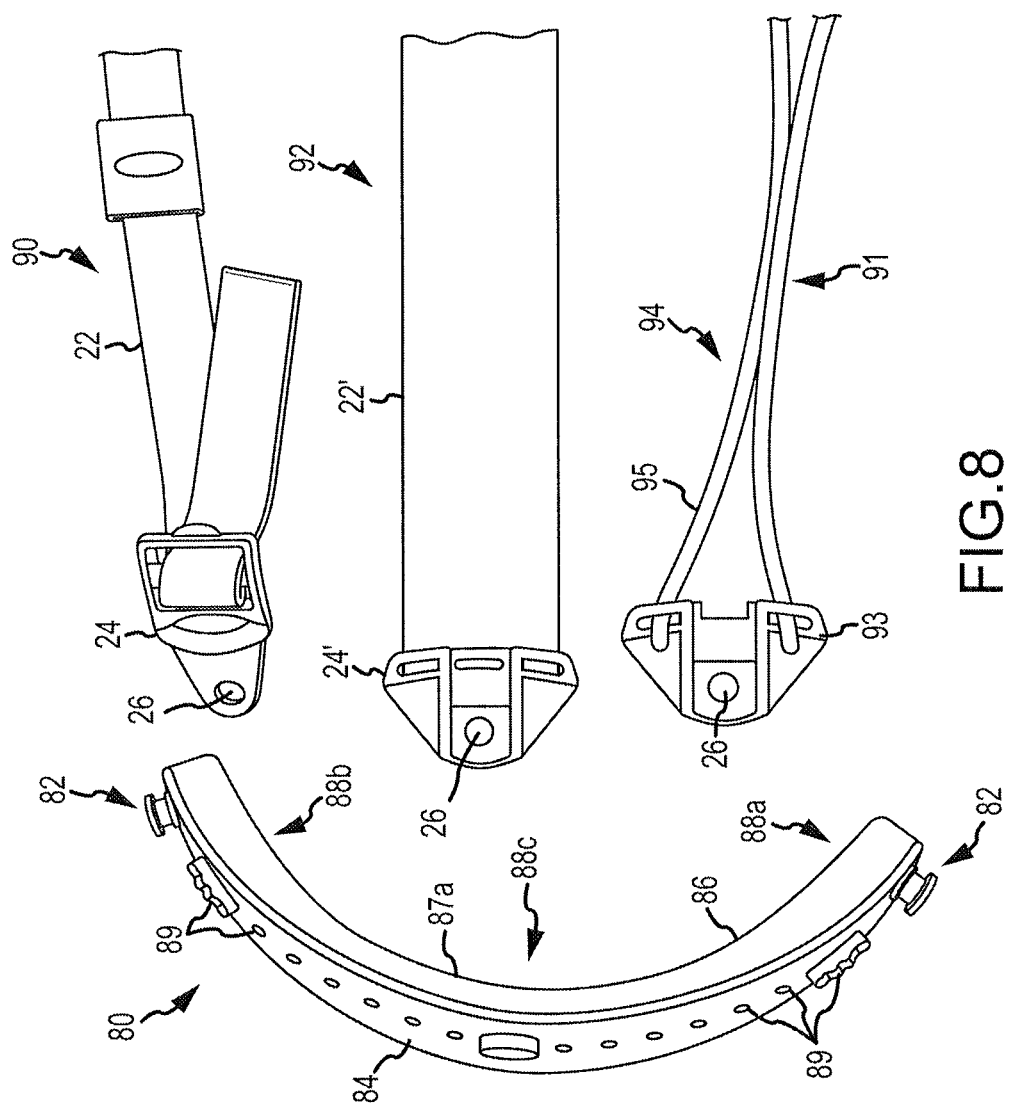
FIG. 8 is a top view of a goggle and a plurality of removable goggle straps for use with strap attachment systems according to some examples herein.
Figure 9A:
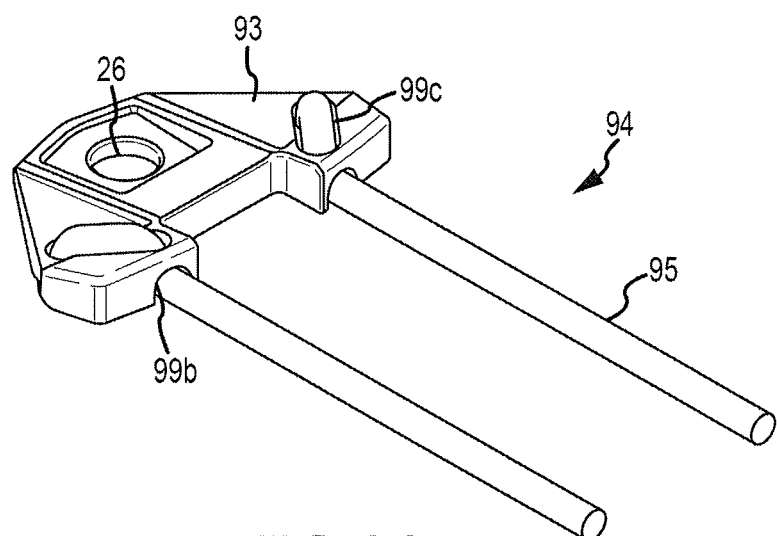
FIGS. 9A and 9B are isometric and bottom views of an example of a strap according to the present disclosure.
Figure 9B:
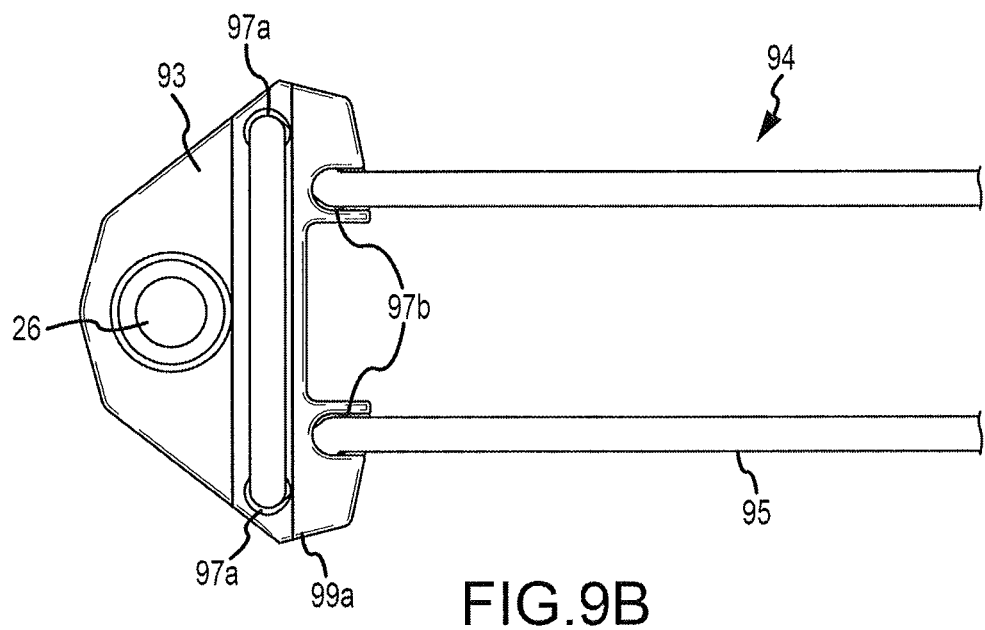

FIGS. 8-10 depict further examples according to the present invention. FIG. 8 shows an example of a goggle 80, which incorporates a strap attachment system 82 according to the present disclosure. The goggle 80 may be configured similar to the goggles described above, and the strap attachment system 82 may be implemented as the strap connector 30 or strap connector 30' in the previous examples. The goggle 80 may include a lens 84 and a contact member 86 attached to the lens. The contact member 86 may be similar to the one or more contact members 16. The contact member 86 in the particular example in FIG. 8 is implemented as a pair of molded foam members (e.g., top foam member 87a and bottom foam member not visible in FIG. 8) with cross section that varies along the length of each foam member. For example, the top foam member 87a may be wider and/or more compliant at the side regions 88a, 88b and narrower and more rigid at an intermediate region 88c. The bottom foam member may similarly be wider in cross section at its respective side regions and may be narrower at a central region (e.g., around the nose recess). The goggle may include additional features, for example a vent mechanism 89. An example vent mechanism that may be used is described in co-pending U.S. patent application Ser. No. 13/186,168, which application is incorporated herein by this reference in its entirety for any purpose.

FIG. 8 further shows a plurality of straps 90, 92, and 94 according to various embodiments of the invention. Each of the straps 90, 92, and 94 may be usable with the strap attachment system 82 of goggle 80. Each of the straps may be implemented in a similar manner as previously described and may include a band and a strap tab. For example, the strap 90 may be similar to the strap 20 and may include a band 22 and strap tab 24 as previously described. According to other examples, the strap may be tailored for a particular fit or application. For example, a wider elastic portion (e.g., elastic band 22') may be used for a more comfortable fit against the back of the user's head or for providing increase friction against whatever surface the strap is placed. Moreover, in some examples, the elastic band 22' may be fixedly attached to the strap tab 24 (e.g., fused thereto) as in the example of strap 92 rather than removably threading the band 22 through a buckle as in the example of strap 90. In yet further examples, the strap 94 may be implemented using an elastic cord and an example of strap 94 is depicted in further detail in FIGS. 9A and 9B. The strap 94 includes an elastic portion 91 which is made of a rounded elastic or bungee cord 95, and the strap further includes strap tab 93. The strap tab 93 includes an arrangement of openings (e.g., 97a, 97b) and grooves (99a, 99b, 99c) for passing the cord 95 therethrough and for seating the cord within the grooves for a low profile fit of the strap 94. As with the previous examples, the strap tab 93 includes an opening 26 as described previously with reference to the earlier figures. The goggle 80 and multiple straps (e.g., one or more of straps 90, 92, 94, or other straps) may be included in a goggle kit.

Figure 10A:
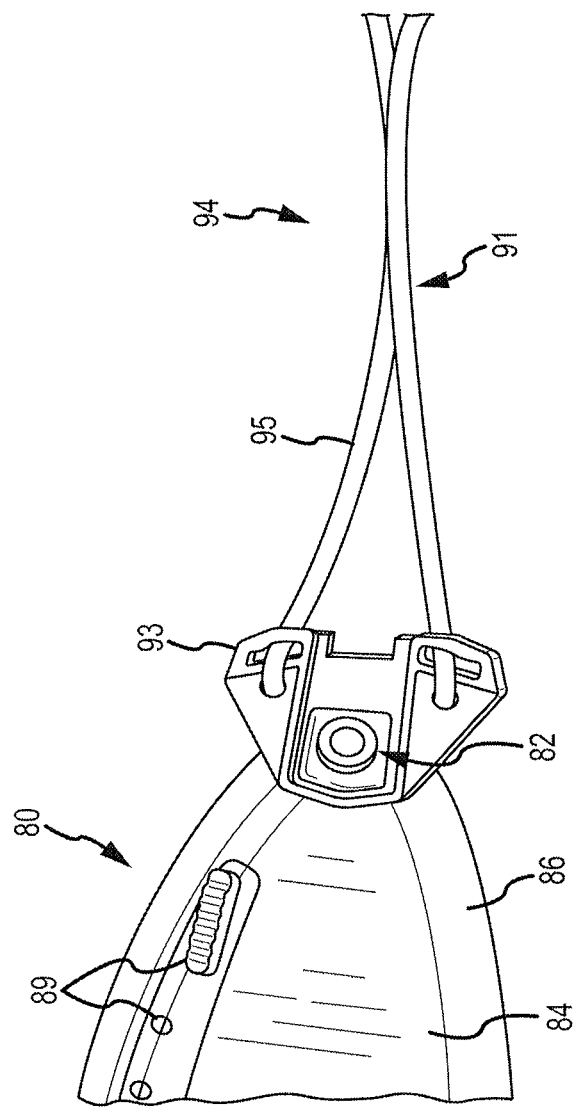
FIGS. 10A-10C are partial front views of the goggle in FIG. 8 shown with each of the plurality of straps attached thereto.
Figure 10B:
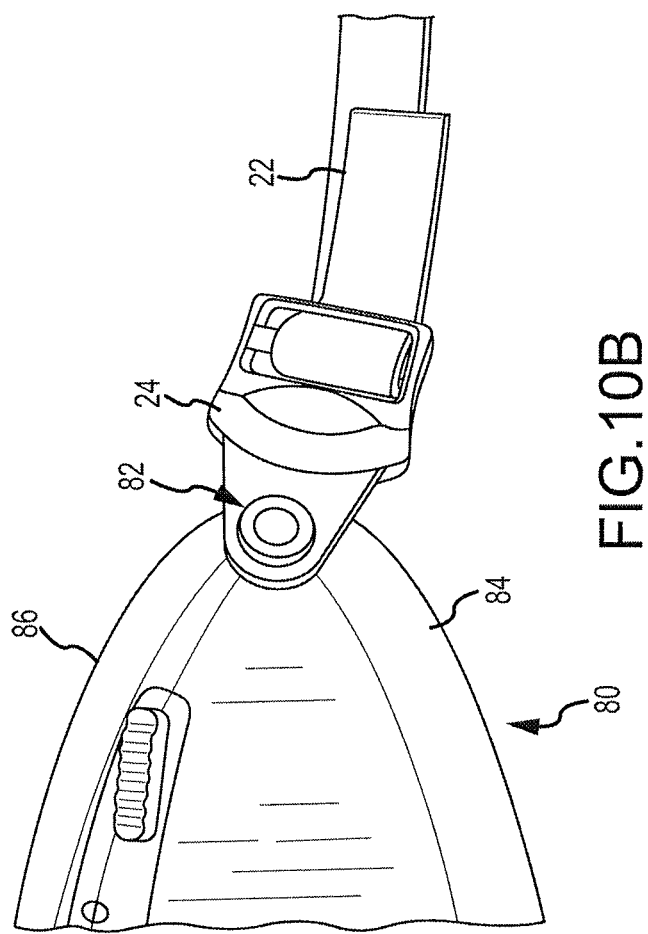
Figure 10C:
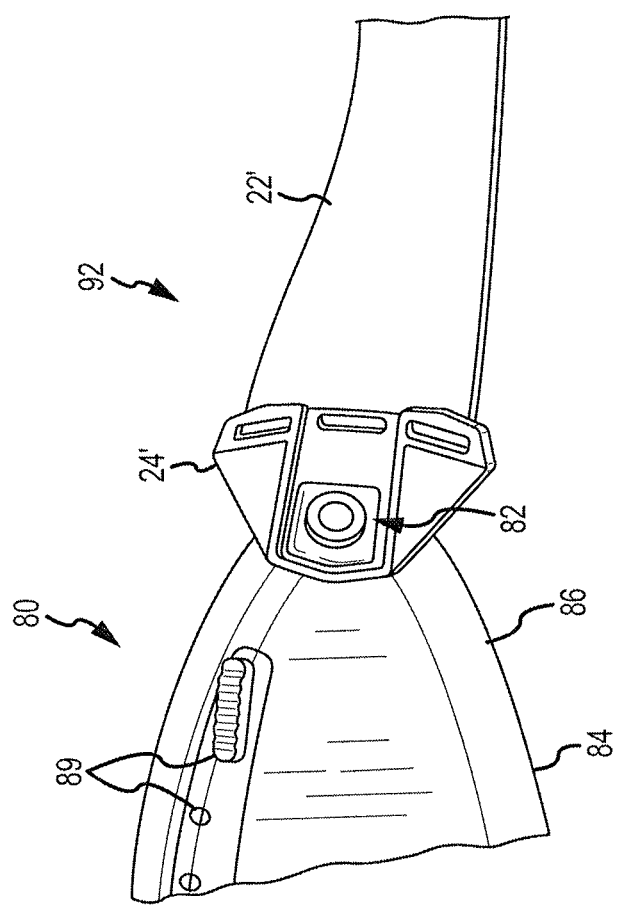

FIGS. 10A-10C show partial front views of the goggle 80 in engagement with each of the straps 90, 92, and 94. Numerous advantages may be achieved with the examples described herein. One advantage is to allow for removable attachment of a goggle strap to the goggle lens, thereby permitting the user to quickly remove and/or exchange the strap with another strap. For example, the strap may become damaged or otherwise unusable for its intended purpose (e.g., the elastic material of the strap may fail causing the strap to be unable to provide a desired amount of tension for securing the goggle to the user's face). In other examples, the user may wish to use the same lens structure, which tends to be the more expensive component in a goggle, with any one of a variety of straps, which may have different sizes, shapes, tension capabilities, wider or lower profiles, etc. The strap attachment systems described herein may facilitate quick and easy interchange of a strap without necessitating a replacement of the goggle.

Although examples of the invention have been described herein, it will be recognized by those skilled in the art to which the invention pertains from a consideration of the foregoing description of presently preferred and alternate embodiments and methods of fabrication and use thereof, and that variations and modifications of this exemplary embodiment and method may be made without departing from the true spirit and scope of the invention. Thus, the above-described embodiments of the invention should not be viewed as exhaustive or as limiting the invention to the precise configurations or techniques disclosed. Rather, it is intended that the invention shall be limited only by the appended claims and the rules and principles of applicable law.

What is claimed is:

1. A goggle comprising:
   a lens;
   a strap connector attached to the lens, the strap connector comprising:
      a button element including:
         a retaining flange;
         a stop flange; and
         a shaft connecting the retaining flange to the stop flange; and
      a post element configured to be coupled to the button element, the post element including:
         a post at least partially received in a passage inside the shaft, wherein the post is configured to pass through the lens; and
         a head coupled to the post at an end of the post opposite the stop flange such that a portion of the lens is disposed between the head and the stop flange; and
   a strap coupled to an attachment portion, the attachment portion configured to be removably coupled to the strap connector between the retaining flange and stop flange of the strap connector, wherein the strap connector remains attached to the lens when the attachment portion is removed from the strap connector.

2. The goggle of claim 1, wherein at least a portion of the strap connector is welded to a portion of the lens.

3. The goggle of claim 1, wherein the interior of the shaft defines a passage which extends through at least a portion of the shaft, the passage configured to engage the post when inserted into the passage to secure the strap connector to the lens.

4. The goggle of claim 1, wherein a diameter of the stop flange is greater than a diameter of a hole formed in the lens.

5. The goggle of claim 3, wherein the post includes an indent and the shaft includes a protrusion in the passage, wherein the protrusion is configured to engage the indent.

6. The goggle of claim 1, wherein the attachment portion includes an opening with a diameter greater than a diameter of the shaft but smaller than a diameter of the retaining flange.

7. The goggle of claim 1, wherein the attachment portion comprises a strap tab made from a flexible material, the strap further comprising a band attached to the strap tab opposite the strap connector.

8. The goggle of claim 7, wherein the band comprises an elastic band.

9. The goggle of claim 1 further comprising a contact member attached to the lens, the contact member configured for placement against a wearer's face to provide the lens in a spaced apart position relative to the wearer's face.

10. The goggle of claim 9, wherein the contact member is an elongate foam member adhered to the lens.

11. The goggle of claim 10, wherein the elongate foam member is a molded foam member, a cross-section of the foam member varying along a length of the foam member.

12. A goggle lens structure comprising:
   a lens;
   a spacer coupled to a perimeter of the lens; and
   a strap attachment system fixedly attached to the lens and configured for removably attaching a strap tab to the strap attachment system, the strap attachment system comprising:
      a button element adjacent to a first surface of the lens, the button element including a retaining flange and a stop flange, wherein the retaining flange and the stop flange are coupled by a shaft; and
      an anchor portion at least partially inserted in the button element, the anchor portion comprising:
         a base adjacent to a second surface of the lens opposite the first surface of the lens; and
         a cylindrical portion extending from the base to the button element.

13. The goggle lens structure of claim 12, wherein the strap attachment system is pivotally coupled to the lens.

14. The goggle lens structure of claim 12, wherein the strap attachment system is press-fit into the lens.

15. The goggle lens structure of claim 12, wherein the lens is a single lens structure.

16. The goggle lens structure of claim 12, wherein the lens further comprises a vent mechanism.

17. The goggle lens structure of claim 12, wherein the anchor portion comprises a plurality of legs configured to be squeezed towards each other during insertion of the anchor portion through the thickness of the lens and to be released upon passing through the thickness of the lens.

* * * * *